(12) United States Patent
Dhulipala et al.

(10) Patent No.: US 9,587,159 B2
(45) Date of Patent: Mar. 7, 2017

(54) ENZYMES FOR REMOVING SULFUROUS COMPOUNDS IN DOWNHOLE FLUIDS

(71) Applicant: BAKER HUGHES INCORPORATED, Houston, TX (US)

(72) Inventors: Prasad D. Dhulipala, Austin, TX (US); Charles D. Armstrong, Tomball, TX (US)

(73) Assignee: Baker Hughes Incorporated, Houston, TX (US)

( * ) Notice: Subject to any disclaimer, the term of this patent is extended or adjusted under 35 U.S.C. 154(b) by 13 days.

(21) Appl. No.: 14/560,762

(22) Filed: Dec. 4, 2014

(65) Prior Publication Data

US 2016/0160105 A1 Jun. 9, 2016

(51) Int. Cl.
*E21B 43/16* (2006.01)
*C09K 8/035* (2006.01)
*C09K 8/532* (2006.01)

(52) U.S. Cl.
CPC .............. *C09K 8/035* (2013.01); *C09K 8/532* (2013.01); *E21B 43/16* (2013.01); *C09K 2208/20* (2013.01)

(58) Field of Classification Search
CPC .... C09K 8/035; C09K 8/532; C09K 2208/20; E21B 43/16
USPC ........................... 166/308.1, 271, 305.1, 246
See application file for complete search history.

(56) References Cited

U.S. PATENT DOCUMENTS

| | | |
|---|---|---|
| 5,247,995 A | 9/1993 | Tjon-Hoe-Pin et al. |
| 6,818,594 B1 * | 11/2004 | Freeman ................ C09K 8/536 166/300 |
| 2003/0013172 A1 * | 1/2003 | Gerendash ........... C12N 9/2417 435/189 |
| 2004/0002075 A1 | 1/2004 | Ishikawa et al. |
| 2010/0163255 A1 | 7/2010 | Horton et al. |
| 2010/0248997 A1 * | 9/2010 | Li ........................ C09K 8/685 507/211 |
| 2011/0056683 A1 | 3/2011 | Duncum et al. |
| 2011/0117067 A1 | 5/2011 | Esteghlalian et al. |

OTHER PUBLICATIONS

Characterization of a Novel Thermostable O-acetylserine sulfhydrylase from Aeropyrum pernix K1, Mino K and Ishikawa K, J. Bacteriology Apr. 2003; 185(7): 2277-84.

Oda. Y. et al., Three-dimensional structure of a new enzyme, O-phosphoserine 1-18 sulfhydrylase, involved in I-cysleine biosynthesis by a hyperthermophilic archaean, Aeropyrum pernix KI , at 2.0 resolution , Journal of Molecular Biology. 2005. vol. 351. No. 2, pp. 334-344.

* cited by examiner

*Primary Examiner* — Doug Hutton, Jr.
*Assistant Examiner* — Silvana Runyan
(74) *Attorney, Agent, or Firm* — Mossman, Kumar & Tyler, P.C.

(57) ABSTRACT

Cysteine synthase or O-Acetyl-L-Serine Sulfhydrylase enzymes, such as those derived from the *Aeropyrum pernix* bacterium, may be used in additive compositions, fluid compositions, and methods for decreasing or removing hydrogen sulfide from recovered downhole fluids and/or the subterranean reservoir wellbore from which the downhole fluid was recovered. The fluid composition may include at least one cysteine synthase enzyme and a base fluid, such as a drilling fluid, a servicing fluid, a production fluid, a completion fluid, an injection fluid, a refinery fluids, and combinations thereof.

5 Claims, 3 Drawing Sheets

```
5'
ATGAGAGGATCGCATCACCATCACCATCACGCGCTGGCGGATATTAGCGGCTATCTGGATGTG
CTGGATAGCGTGCGCGGCTTTAGCTATCTGGAAAACGCGCGCGAAGTGCTGCGCAGCGGCGA
AGCGCGCTGCCTGGGCAACCCGCGCAGCGAACCGGAATATGTGAAAGCGCTGTATGTGATTG
GCGCGAGCCGCATTCCGGTGGGCGATGGCTGCAGCCATACCCTGGAAGAACTGGGCGTGTTT
GATATTAGCGTGCCGGGCGAAATGGTGTTTCCGAGCCCGCTGGATTTTTTTGAACGCGGCAAA
CCGACCCCGCTGGTGCGCAGCCGCCTGCAGCTGCCGAACGGCGTGCGCGTGTGGCTGAAACT
GGAATGGTATAACCCGTTTAGCCTGAGCGTGAAAGATCGCCCGGCGGTGGAAATTATTAGCC
GCCTGAGCCGCCGCGTGGAAAAAGGCAGCCTGGTGGCGGATGCGACCAGCAGCAACTTTGGC
GTGGCGCTGAGCGCGGTGGCGCGCCTGTATGGCTATCGCGCGCGCGTGTATCTGCCGGGCGCG
GCGGAAGAATTTGGCAAACTGCTGCCGCGCCTGCTGGGCGCGCAGGTGATTGTGGATCCGGA
AGCGCCGAGCACCGTGCATCTGCTGCCGCGCGTGATGAAAGATAGCAAAAACGAAGGCTTTG
TGCATGTGAACCAGTTTTATAACGATGCGAACTTTGAAGCGCATATGCGCGGCACCGCGCGCG
AAATTTTTGTGCAGAGCCGCCGCGGCGGCCTGGCGCTGCGCGGCGTGGCGGGCAGCCTGGGC
ACCAGCGGCCATATGAGCGCGGCGGCGTTTTATCTGCAGAGCGTGGATCCGAGCATTCGCGCG
GTGCTGGTGCAGCCGGCGCAGGGCGATAGCATTCCGGGCATTCGCCGCGTGGAAACCGGCAT
GCTGTGGATTAACATGCTGGATATTAGCTATACCCTGGCGGAAGTGACCCTGGAAGAAGCGAT
GGAAGCGGTGGTGGAAGTGGCGCGCAGCGATGGCTGGTGATTGGCCCGAGCGGCGGCGCGG
CGGTGAAAGCGCTGGCGAAAAAAGCGGCGGAAGGCGATCTGGAACCGGGCGATTATGTGGTG
GTGGTGCCGGATACCGGCTTTAAATATCTAGCCTGGTGCAGAACGCGCTGGAAGGCGCGGGC
GATAGCGTGTAA
--3'
```

5'
ATGAGAGGATCGCATCACCATCACCATCACGCGCTGGCGGATATTAGCGGCTATCTGGATGTG
CTGGATAGCGTGCGCGGCTTTAGCTATCTGGAAAACGCGCGCGAAGTGCTGCGCAGCGGCGA
AGCGCGCTGCCTGGGCAACCCGCGCAGCGAACCGGAATATGTGAAAGCGCTGTATGTGATTG
GCGCGAGCCGCATTCCGGTGGGCGATGGCTGCAGCCATACCCTGGAAGAACTGGGCGTGTTT
GATATTAGCGTGCCGGGCGAAATGGTGTTTCCGAGCCCGCTGGATTTTTTTGAACGCGGCAAA
CCGACCCCGCTGGTGCGCAGCCGCCTGCAGCTGCCGAACGGCGTGCGCGTGTGGCTGAAACT
GGAATGGTATAACCCGTTTAGCCTGAGCGTGAAAGATCGCCCGGCGGTGGAAATTATTAGCC
GCCTGAGCCGCCGCGTGGAAAAAGGCAGCCTGGTGGCGGATGCGACCAGCAGCAACTTTGGC
GTGGCGCTGAGCGCGGTGGCGCGCCTGTATGGCTATCGCGCGCGCGTGTATCTGCCGGGCGCG
GCGGAAGAATTTGGCAAACTGCTGCCGCGCCTGCTGGGCGCGCAGGTGATTGTGGATCCGGA
AGCGCCGAGCACCGTGCATCTGCTGCCGCGCGTGATGAAAGATAGCAAAAACGAAGGCTTTG
TGCATGTGAACCAGTTTTATAACGATGCGAACTTTGAAGCGCATATGCGCGGCACCGCGCGCG
AAATTTTTGTGCAGAGCCGCCGCGGCGGCCTGGCGCTGCGCGGCGTGGCGGGCAGCCTGGGC
ACCAGCGGCCATATGAGCGCGGCGGCGTTTTATCTGCAGAGCGTGGATCCGAGCATTCGCGCG
GTGCTGGTGCAGCCGGCGCAGGGCGATAGCATTCCGGGCATTCGCCGCGTGGAAACCGGCAT
GCTGTGGATTAACATGCTGGATATTAGCTATACCCTGGCGGAAGTGACCCTGGAAGAAGCGAT
GGAAGCGGTGGTGGAAGTGGCGCGCAGCGATGGCCTGGTGATTGGCCCGAGCGGCGGCGCGG
CGGTGAAAGCGCTGGCGAAAAAAGCGGCGGAAGGCGATCTGGAACCGGGCGATTATGTGGTG
GTGGTGCCGGATACCGGCTTTAAATATCTAGCCTGGTGCAGAACGCGCTGGAAGGCGCGGGC
GATAGCGTGTAA
--3'

SEQUENCE LISTING

```
<160> NUMBER OF SEQ ID NOS: 1

<210> SEQ ID NO 1
<211> LENGTH: 1196
<212> TYPE: DNA
<213> ORGANISM: Aeropyrum pernix

<400> SEQUENCE: 1
atgagaggat cgcatcacca tcaccatcac gcgctggcgg atattagcgg ctatctggat      60
```

```
gtgctggata gcgtgcgcgg ctttagctat ctggaaaacg cgcgcgaagt gctgcgcagc    120
ggcgaagcgc gctgcctggg caacccgcgc agcgaaccgg aatatgtgaa agcgctgtat    180
gtgattggcg cgagccgcat tccggtgggc gatggctgca gccatacccct ggaagaactg    240 ggcgtgtttg atattagcgt gccgggcgaa atggtgtttc cgagcccgct ggatttttt     300 gaacgcggca aaccgacccc gctggtgcgc agccgcctgc agctgccgaa cggcgtgcgc    360
gtgtggctga aactggaatg gtataacccg tttagcctga gcgtgaaaga tcgcccggcg    420
gtggaaatta ttagccgcct gagccgccgc gtggaaaaag gcagcctggt ggcggatgcg    480
accagcagca actttggcgt ggcgctgagc gcggtggcgc gcctgtatgg ctatcgcgcg    540
cgcgtgtatc tgccgggcgc ggcggaagaa tttggcaaac tgctgccgcg cctgctgggc    600
gcgcaggtga ttgtggatcc ggaagcgccg agcaccgtgc atctgctgcc gcgcgtgatg    660
aaagatagca aaaacgaagg ctttgtgcat gtgaaccagt tttataacga tgcgaacttt    720
gaagcgcata tgcgcggcac cgcgcgcgaa attttttgtgc agagccgccg cggcggcctg    780
gcgctgcgcg gcgtggcggg cagcctgggc accagcggcc atatgagcgc ggcggcgttt    840
tatctgcaga gcgtggatcc gagcattcgc gcggtgctgg tgcagccggc gcagggcgat    900
agcattccgg gcattcgccg cgtggaaacc ggcatgctgt ggattaacat gctggatatt    960
agctataccc tggcggaagt gaccctggaa gaagcgatgg aagcggtggt ggaagtggcg   1020
cgcagcgatg gcctggtgat tggcccgagc ggcggcgcgg cggtgaaagc gctggcgaaa   1080
aaagcggcgg aaggcgatct ggaaccgggc gattatgtgg tggtggtgcc ggataccggc   1140
tttaaatatc tagcctggtg cagaacgcgc tggaaggcgc gggcgatagc gtgtaa        1196
```

ENZYMES FOR REMOVING SULFUROUS COMPOUNDS IN DOWNHOLE FLUIDS

TECHNICAL FIELD

The present invention relates to additive compositions, fluid compositions, and methods for using at least one cysteine synthase enzyme in a downhole fluid, and more specifically relates to decreasing or removing hydrogen sulfide using at least one cysteine synthase enzyme, such as those derived from *Aeropyrum pernix*.

BACKGROUND

The presence of sulfur species in hydrocarbon fluids and aqueous streams is undesirable for various reasons. The subterranean reservoirs currently being developed have increased amounts of sulfur species within the produced hydrocarbon streams (oil and gas). Hydrogen sulfide is a toxic gas that is heavier than air and is very corrosive to well and surface equipment.

During combustion, sulfur-rich hydrocarbon streams also produce heavy environmental pollution. When sulfur-rich streams contact metals, sulfur species lead to brittleness in carbon steels and to stress corrosion cracking in more highly alloyed materials. Moreover, hydrogen sulfides in various hydrocarbon or aqueous streams pose a safety hazard and a corrosion hazard. A quick removal of these odorous and environmentally malicious species would be desirable in both oilfield and refinery operations.

For the reasons mentioned, attempts have been made to wash out, or chemically convert, the sulfur species from hydrocarbon fluids and aqueous systems. Several classes of chemicals, also known as sweeteners, are available for removing sulfur species from a hydrocarbon or aqueous stream, but many of them have serious limitations. For example, nitrogen-containing hydrogen sulfide sweeteners, such as hydrotriazine-based additives, have been in the industry for a long while now. However, the amines released while scavenging the sulfur species pose an overhead corrosion threat in various downstream processes, including distillation columns. Formaldehyde is a nitrogen-free sweetener, but it is also a potential carcinogen. Glyoxal is another nitrogen-free hydrogen sulfide sweetener, but its application is often limited due to its corrosivity and low boiling point. Metal oxides have also been proposed, but such applications are narrowed by the handling challenges and solid residual formation concerns to downstream refining catalysts and processes. Acrolein is a clean and extremely potent hydrogen sulfide/mercaptan sweetener, but it requires special handling due to toxicity concerns.

Sulfur-containing compounds are deleterious in the subterranean reservoir wellbores in which they reside. Additives may be added to the downhole fluids for circulation into the reservoir wellbore. The downhole fluids may be or include drilling fluids, completion fluids, servicing fluids (e.g. fracturing fluids), production fluids, injection fluids, and combinations thereof. Drilling fluids are typically classified according to their base fluid. In water-based fluids, solid particles, such as weighting agents, are suspended in a continuous phase consisting of water or brine. Oil can be emulsified in the water, which is the continuous phase. "Water-based fluid" is used herein to include fluids having an aqueous continuous phase where the aqueous continuous phase can be all water or brine, an oil-in-water emulsion, or an oil-in-brine emulsion. Brine-based fluids, of course are water-based fluids, in which the aqueous component is brine.

Oil-based fluids are the opposite or inverse of water-based fluids. "Oil-based fluid" is used herein to include fluids having a non-aqueous continuous phase where the non-aqueous continuous phase is all oil, a non-aqueous fluid, a water-in-oil emulsion, a water-in-non-aqueous emulsion, a brine-in-oil emulsion, or a brine-in-non-aqueous emulsion. In oil-based fluids, solid particles are suspended in a continuous phase consisting of oil or another non-aqueous fluid. Water or brine can be emulsified in the oil; therefore, the oil is the continuous phase. In oil-based fluids, the oil may consist of any oil or water-immiscible fluid that may include, but is not limited to, diesel, mineral oil, esters, refinery cuts and blends, or alpha-olefins. Oil-based fluid as defined herein may also include synthetic-based fluids or muds (SBMs), which are synthetically produced rather than refined from naturally-occurring materials. Synthetic-based fluids often include, but are not necessarily limited to, olefin oligomers of ethylene, esters made from vegetable fatty acids and alcohols, ethers and polyethers made from alcohols and polyalcohols, paraffinic, or aromatic, hydrocarbons alkyl benzenes, terpenes and other natural products and mixtures of these types.

There are a variety of functions and characteristics that are expected of completion fluids. The completion fluid may be placed in a well to facilitate final operations prior to initiation of production. Completion fluids are typically brines, such as chlorides, bromides, and/or formates, but may be any non-damaging fluid having proper density and flow characteristics. Suitable salts for forming the brines include, but are not necessarily limited to, sodium chloride, calcium chloride, zinc chloride, potassium chloride, potassium bromide, sodium bromide, calcium bromide, zinc bromide, sodium formate, potassium formate, ammonium formate, cesium formate, and mixtures thereof. Chemical compatibility of the completion fluid with the reservoir formation and formation fluids is key. Chemical additives, such as polymers and surfactants are known in the art for being introduced to the brines used in well servicing fluids for various reasons that include, but are not limited to, increasing viscosity, and increasing the density of the brine. Completion fluids do not contain suspended solids.

Production fluid is the fluid that flows from a formation to the surface of an oil well. These fluids may include oil, gas, water, as well as any contaminants (e.g. $H_2S$, asphaltenes, etc.). The consistency and composition of the production fluid may vary.

Refinery fluids are fluids that may be further processed or refined at a refinery. A non-limiting example of a refinery process may include reducing or preventing the formation of foulants. Non-limiting examples of foulants may be or include hydrates, asphaltenes, coke, coke precursors, naphthenates, inorganic solid particles (e.g. sulfates, oxides, scale, and the like), and combinations thereof. Non-limiting examples of fluids to be refined include crude oil, production water, and combinations thereof.

Servicing fluids, such as remediation fluids, stimulation fluids, workover fluids, and the like, have several functions and characteristics necessary for repairing a damaged well. Such fluids may be used for breaking emulsions already formed and for removing formation damage that may have occurred during the drilling, completion and/or production operations. The terms "remedial operations" and "remediate" are defined herein to include a lowering of the viscosity of gel damage and/or the partial or complete removal of damage of any type from a subterranean formation. Similarly, the term "remediation fluid" is defined herein to include any fluid that may be useful in remedial operations. A stimulation fluid may be a treatment fluid prepared to stimulate, restore, or enhance the productivity of a well, such as fracturing fluids and/or matrix stimulation fluids in one non-limiting example.

Hydraulic fracturing is a type of stimulation operation, which uses pump rate and hydraulic pressure to fracture or crack a subterranean formation in a process for improving the recovery of hydrocarbons from the formation. Once the crack or cracks are made, high permeability proppant relative to the formation permeability is pumped into the fracture to prop open the crack. When the applied pump rates and pressures are reduced or removed from the formation, the crack or fracture cannot close or heal completely because the high permeability proppant keeps the crack open. The propped crack or fracture provides a high permeability path connecting the producing wellbore to a larger formation area to enhance the production of hydrocarbons.

The development of suitable fracturing fluids is a complex art because the fluids must simultaneously meet a number of conditions. For example, they must be stable at high temperatures and/or high pump rates and shear rates that can cause the fluids to degrade and prematurely settle out the proppant before the fracturing operation is complete. Various fluids have been developed, but most commercially used fracturing fluids are aqueous based liquids that have either been gelled or foamed to better suspend the proppants within the fluid.

Injection fluids may be used in enhanced oil recovery (EOR) operations, which are sophisticated procedures that use viscous forces and/or interfacial forces to increase the hydrocarbon production, e.g. crude oil, from oil reservoirs. The EOR procedures may be initiated at any time after the primary productive life of an oil reservoir when the oil production begins to decline. The efficiency of EOR operations may depend on reservoir temperature, pressure, depth, net pay, permeability, residual oil and water saturations, porosity, fluid properties, such as oil API gravity and viscosity, and the like.

EOR operations are considered a secondary or tertiary method of hydrocarbon recovery and may be necessary when the primary and/or secondary recovery operation has left behind a substantial quantity of hydrocarbons in the subterranean formation. Primary methods of oil recovery use the natural energy of the reservoir to produce oil or gas and do not require external fluids or heat as a driving energy; EOR methods are used to inject materials into the reservoir that are not normally present in the reservoir.

Secondary EOR methods of oil recovery inject external fluids into the reservoir, such as water and/or gas, to re-pressurize the reservoir and increase the oil displacement. Tertiary EOR methods include the injection of special fluids, such as chemicals, miscible gases and/or thermal energy. The EOR operations follow the primary operations and target the interplay of capillary and viscous forces within the reservoir. For example, in EOR operations, the energy for producing the remaining hydrocarbons from the subterranean formation may be supplied by the injection of fluids into the formation under pressure through one or more injection wells penetrating the formation, whereby the injection fluids drive the hydrocarbons to one or more producing wells penetrating the formation. EOR operations are typically performed by injecting the fluid through the injection well into the subterranean reservoir to restore formation pressure, improve oil displacement or fluid flow in the reservoir, and the like.

Examples of EOR operations include water-based flooding and gas injection methods. Water-based flooding may also be termed 'chemical flooding' if chemicals are added to the water-based injection fluid. Water-based flooding may be or include, polymer flooding, ASP (alkali/surfactant/polymer) flooding, SP (surfactant/polymer) flooding, low salinity water and microbial EOR; gas injection includes immiscible and miscible gas methods, such as carbon dioxide flooding, and the like.

It would be desirable if additives were developed for fluid compositions used during hydrocarbon recovery to decrease or remove sulfur-containing compounds in recovered downhole fluids and in hydrocarbon reservoir wellbores.

SUMMARY

There is provided, in one form, an additive composition to be added to a base fluid, such as but not limited to, a drilling fluid, a completion fluid, a production fluid, a servicing fluid, an injection fluid, a refinery fluid, and combinations thereof. The additive may have or include at least one cysteine synthase enzyme that is at least 75% homologous to the cDNA sequence of SEQ ID NO:1.

There is provided, in a non-limiting form, a fluid composition having a base fluid and at least one cysteine synthase enzyme that is at least 75% homologous to the cDNA sequence of SEQ ID NO:1. The base fluid may be or include, but is not limited to, drilling fluids, servicing fluids, production fluids, completion fluids, injection fluids, refinery fluids, and combinations thereof.

There is further provided in an alternative non-limiting embodiment of a method that may include circulating a fluid composition into a subterranean reservoir wellbore and decreasing an amount of sulfur-containing compounds in the subterranean reservoir wellbore and/or in a downhole fluid recovered from a subterranean reservoir wellbore. The fluid composition may have or include at least one cysteine synthase enzyme that is at least 75% homologous to the cDNA sequence of SEQ ID NO:1 in an effective concentration to decrease an amount of sulfur-containing compounds.

The cysteine synthase enzyme appears to remove hydrogen sulfide from recovered downhole fluids and/or in subterranean reservoir wellbores.

BRIEF DESCRIPTION OF THE DRAWINGS

In order to more fully understand the drawings referred to in the detailed description, a brief description of each drawing is presented here:

FIG. 5 is a graph depicting an amount of $H_2S$ measured in head space after treating a bottle or condition containing It has been discovered that an additive composition having a cysteine synthase derived from *Aeropyrum pernix* may be added to a base fluid to decrease an amount of sulfur-species in the base fluid. Alternatively, a fluid composition comprising a cysteine synthase derived from *Aeropyrum pernix* may be circulated in a subterranean reservoir wellbore to decrease an amount of sulfur-species compounds present in the subterranean reservoir wellbore and/or any downhole fluids recovered therefrom. In addition to being biodegradable, the cysteine synthase enzyme may be less toxic to the environment and may be made from renewable resources. The use of cysteine synthase enzymes in a base fluid may provide a renewable alternative to conventional additives (non-biodegradable) that are used in downhole fluids to decrease sulfur-containing compounds. In a non-limiting embodiment, the cysteine synthase may be or include, but is not limited to, O-Acetyl-Serine Sulfhydrylase (OASS).

The additive and/or fluid composition may further include an additional component, such as but not limited to, a pyridoxal phosphate, O-acetyl-serine, DTT, and combinations thereof; the additional component(s) may be added to the base fluid at the same time or a different time from the cysteine synthase enzyme. In a non-limiting embodiment, the pyridoxal phosphate may be added to the base fluid in a concentration ranging from about 0.1 mM independently to about 5 mM, alternatively from about 1 mM independently to about 4 mM. In a non-limiting embodiment, the additive and/or fluid composition does not include pyridoxal phosphate. In another non-limiting embodiment, the DTT may be added to the base fluid in a concentration ranging from about 0.25 mM independently to about 5 mM, alternatively from about 1 mM independently to about 3 mM.

In a non-limiting embodiment, the O-acetyl-serine (OAS) may be added to the base fluid in a concentration that is substantially equal to or more than the amount of suspected hydrogen sulfide present in the base fluid and/or the subterranean reservoir wellbore. In an alternative non-limiting embodiment, the OAS may be added to the base fluid in a concentration ranging from about 1 mM independently to about 20 mM, alternatively from about 5 mM independently to about 15 mM.

Cysteine synthase enzymes may remove or decrease sulfur-containing compounds, e.g. hydrogen sulfide ($H_2S$) in a non-limiting embodiment, within a recovered downhole fluid from a subterranean reservoir wellbore and/or decrease the amount of hydrogen sulfide or other sulfur-containing compounds in the wellbore from which the downhole fluid was recovered. The cysteine synthase enzyme may catalyze the reaction of an O-acetyl-L-serine and hydrogen sulfide to form L-cysteine and acetate. In a non-limiting embodiment, hydrogen sulfide is converted into L-cysteine in a 1:1 ratio, i.e. one mole of $H_2S$ forms one mole of L-cysteine. Likewise, O-acetyl-L-serine and hydrogen bind to the enzyme in a 1:1 ratio.

'Cysteine synthase enzyme' is defined herein to be the active site of the cysteine synthase enzyme to convert hydrogen sulfide into L-cysteine and acetate. The active site may be or include the whole protein, an active fragment of the protein, a mimetic of the protein, and combinations thereof. 'Fragment' as used herein is meant to include any amino acid sequence shorter than the full-length cysteine synthase enzyme, but where the fragment maintains similar activity to the full-length cysteine synthase enzyme. Fragments may include a single contiguous sequence identical to a portion of the cysteine synthase enzyme sequence. Alternatively, the fragment may have or include several different shorter segments where each segment is identical in amino acid sequence to a different portion of the amino acid sequence of the cysteine synthase enzyme, but linked via amino acids differing in sequence from the cysteine synthase enzyme. 'Mimetic' as used herein may include polypeptides, which may be recombinant, and peptidomimetics, as well as small organic molecules, which exhibit similar or enhanced catalytic activity as compared to the cysteine synthase enzyme described herein.

Figure 1:
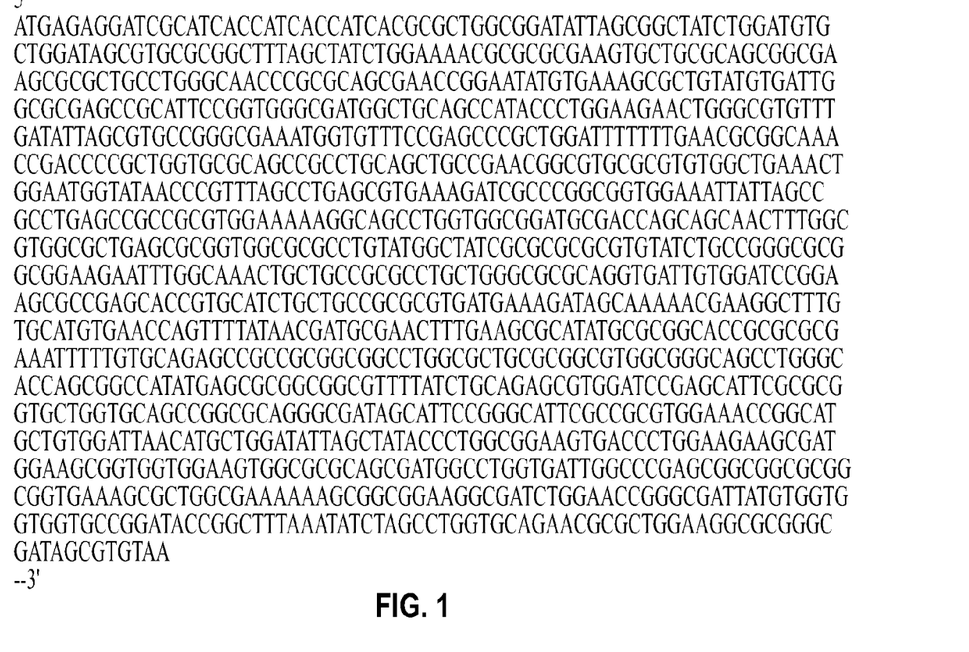
FIG. 1 (SEQ ID NO:1) represents the nucleotide sequence that codes for the cysteine synthase enzyme.

The gene for the cysteine synthase enzyme may be codon optimized to increase the efficiency of its expression in *E. coli*. The nucleotide sequence of one embodiment of the cysteine synthase enzyme is set forth in FIG. 1 (SEQ ID NO:1). The gene coding for the cysteine synthase enzyme may have a nucleotide sequence that is substantially homologous to the nucleotide sequence of FIG. 1 (SEQ ID NO:1). The term "substantially homologous" is used herein to denote nucleotides having at least 75% sequence identity to the sequence shown in FIG. 1 (SEQ ID NO:1), alternatively from about 80% independently to about 99.5%, or from about 85% independently to about 95%. As used herein with respect to a range, "independently" means that any threshold may be used together with another threshold to give a suitable alternative range, e.g. about 75% independently to about 85% is also considered a suitable alternative range.

The cysteine synthase enzyme may be a homodimer, i.e. two subunits that are the same, where each subunit may have a pyridoxal phosphate as a cofactor. However, as previously mentioned, the cysteine synthase enzyme may function in the absence of a pyridoxal phosphate cofactor.

The primary structural sequence is the linear sequence of amino acids that are linked together by peptide bonds to form the primary structure of the cysteine synthase enzyme. The secondary structure of the protein refers to the base pairing interactions within a single molecule or set of interacting molecules, such as a beta-helix in the cysteine synthase enzyme. Tertiary structure refers to the three-dimensional structure of the cysteine synthase enzyme formed from the nucleotide sequence. Quaternary structure refers to the interaction between at least two tertiary structures.

To obtain the cysteine synthase enzyme, the *Aeropyrum pernix* bacterium may be plated on a growth medium, such as an agar, which is conducive to the growth of the *Aeropyrum pernix* bacterium in a non-limiting embodiment. The cysteine synthase enzyme may be directly isolated from the *Aeropyrum pernix* to be added to or used within a fluid composition for decreasing a sulfur-containing compound in a fluid composition and/or a subterranean reservoir wellbore. 'Isolated' is defined herein to denote that the cysteine synthase enzyme has been removed from the intact cells or cellular debris, and is in a condition other than its native environment, is free of other extraneous or unwanted nucleic acids, proteases, and lipids, in a form suitable for use as a cysteine synthase enzyme as described herein.

In a non-limiting embodiment, the cysteine synthase gene of the *Aeropyrum pernix* bacterium may be inserted into a plasmid vector. A vector is a DNA molecule that may be used as a vehicle to artificially carry genetic material from a foreign cell and/or organism. A plasmid is defined as a circular extrachromosomal element found naturally in bacteria and some other organisms, which may be genetically engineered to clone DNA fragments. The plasmid may then be inserted into a host bacterium cell, such as *Escherichia coli*, where the host cell may replicate and/or express the foreign DNA. The *E. coli* cells may be plated on a growth medium, such as an agar, which is conducive to the growth of *E. coli*. The growth of *E. coli* propagates the cysteine synthase enzyme as clones within each *E. coli* cell. The cysteine synthase enzyme may be isolated from the *E. coli* cells and added to or used within a fluid composition.

Figure 2:
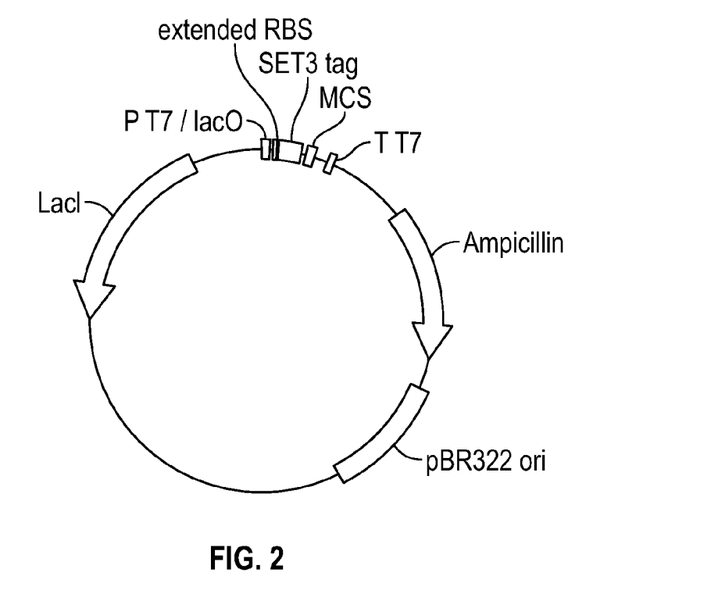
FIG. 2 represents the plasmid pBEn-SET3a used for expressing the cysteine synthase enzyme.

FIG. 2 is a depiction of the plasmid pBEn-SET3a before cloning the cysteine synthase thereinto. P T7/lacO is a promoter site with a lac operator, which is a site for starting transcription. The extended RBS is a ribosomal binding site that is a sequence on mRNA that is bound by a ribosome when initiating protein translation.

The SET3tag may increase the solubility of any problem proteins within *E. coli*. Although the mechanism by which the SET tag may improve solubility has not been confirmed, the SET tag may enhance solubility of the fusion protein by providing a net negative charge, which is thought to prevent aggregation and provide more time for correct protein folding in vivo.

The multiple cloning site (MCS) is a short segment of DNA that has several restriction sites, such as Nde1 and BamH1 in a non-limiting embodiment. Nde1 is a type II restriction enzyme that may cut open specific sequence targets; specifically, Nde1 may be used to cut open the reading frames in the plasmid to insert the cysteine synthase enzyme genes. BamHI is also a type II restriction endonuclease that recognizes the sequence 5'-GGATCC-3', and cleaves these sequences just after the 5'-guanine on each strand to leave sticky ends that are 4 base pairs long.

Ampicillin ($Amp^R$) regulates the expression of β-lactamase, pBR322 ori is the DNA sequence that signals for the origin of replication (also known as 'origin'), and lacI codes for the lactose repressor.

To isolate or obtain the cysteine synthase enzyme from *E. coli*, the *E. coli* cells may be harvested via centrifugation to produce a cell pellet. The cell pellet may be lysed either by physical means or by chemical means, such as detergents and/or enzymes (e.g. lysozyme) to produce a lysate. The raw lysate may contain the recombinant protein, as well as other proteins originating from the bacterial host.

The cysteine synthase enzyme may be in a powder form and/or a liquid form (e.g. in solution) when added to or included in the base fluid. The cysteine synthase enzyme may be part of an additive where the additive includes the cysteine synthase enzyme, as well as other components to aid the cysteine synthase enzyme in decreasing the amount of sulfur-containing compounds in a fluid composition and/or a subterranean reservoir wellbore.

The additive may include a cysteine synthase enzyme that is at least 75% homologous to the cDNA sequence of SEQ ID NO:1. cDNA is defined herein as DNA synthesized from a messenger RNA (mRNA) template in an enzymatic catalyzed reaction using reverse transcriptase. The additive may include the cysteine synthase enzyme within the additive composition in a concentration ranging from about 1 nanomolar (nM) independently to about 5 millimolar (mm), alternatively from about 10 nM independently to about 1 mm, or from about 1 micromolar (μM) independently to about 5 (μM) as compared to the total base fluid.

In a non-limiting embodiment, the reaction may occur for at least 30 minutes, alternatively from about 30 minutes independently to about 4 hours, or from about 1 hour independently to about 4 hours. In a non-limiting embodiment, the cysteine synthase enzyme may maintain optimal function at a temperature ranging from about 75° F. independently to about 180° F., alternatively from about 100° F. independently to about 160° F. The cysteine synthase enzyme may maintain optimal function at a pressure less than about 15,000 pounds per square inch (psi). The cysteine synthase enzyme may maintain optimal function at a pH ranging from about 4 independently to about 11, alternatively from about 5 independently to about 8. The cysteine synthase enzyme may still function at a decreased reaction rate, if at all, outside of the ranges mentioned for temperature, pressure, and/or pH.

The additive may be added to a base fluid to form a fluid composition. The base fluid may be or include, but is not limited to, a drilling fluid, a completion fluid, a production fluid, a servicing fluid, an injection fluid, a refinery fluid, and combinations thereof. In a non-limiting embodiment, the base fluid may be an aqueous fluid, a non-aqueous fluid, and combinations thereof. In another non-limiting embodiment, the base fluid or fluid composition may be contained in an oil pipeline, gas pipeline, a refinery (e.g. separation vessels, dehydration units, gas lines, and pipelines), and combinations thereof.

The fluid composition comprising at least one cysteine synthase that is at least 75% homologous to the cDNA sequence of SEQ ID NO:1 may be circulated into a subterranean reservoir wellbore to decrease an amount of sulfur-containing compounds within the subterranean reservoir wellbore and/or any downhole fluids recovered therefrom. In yet another non-limiting embodiment, the fluid composition may include a salt, such as but not limited to, a brine, sea salt, and combinations thereof. The brine may be or include, but is not limited to potassium chloride, sodium chloride, calcium chloride, zinc chloride, potassium bromide, sodium bromide, calcium bromide, zinc bromide, sodium formate, potassium formate, ammonium formate, cesium formate, and combinations thereof.

'Derived from' with respect to the cysteine synthase enzyme is meant to include whole cysteine synthase enzymes or cysteine synthase enzyme fragments, where the cysteine synthase enzyme originated from *Aeropyrum pernix* bacterium and was isolated from that particular species; 'derived from' also encompasses polypeptides identical in DNA and/or amino acid sequence to the active site (e.g. the cleft between C and N terminal domains and Lysine 47 site in a non-limiting example) of the *Aeropyrum pernix* bacterium that are recombinantly expressed in a host cell expression system or chemically synthesized. 'Recombinant DNA' is DNA that has been formed artificially by combining constituents from different organisms, such as inserting the cysteine synthase enzyme into an *E. coli* host cell for a cloned reproduction of the cysteine synthase enzyme in a non-limiting example.

'Derived from' also includes derivatives of the *Aeropyrum pernix* cysteine synthase enzymes, such as a polypeptide or fragment that may be substantially similar in primary structural sequence to a cysteine synthase enzyme described herein, but which may include chemical and/or biochemical modifications that are not found in the native polypeptide. Such modifications may be or include, but are not limited to a label, such as a radioactive isotope, a fluorophore, or an enzymatic label useful in tracing the cysteine synthase enzyme. The label or other modification may be useful in isolating the cysteine synthase enzyme from the *Aeropyrum pernix* bacterium and/or other expression system (*E. coli* as described below). The label or other modification may be used to identify the cysteine synthase enzyme once the downhole fluid composition needs to be recovered from a subterranean reservoir wellbore and/or recovering the cysteine synthase enzyme from the fluid composition. Other non-limiting modifications may be or include a nucleotide mutagenesis to impart additional thermostability and pH tolerance to the cysteine synthase enzyme.

The method may include decreasing the amount of at least one sulfur-containing compound within the fluid composition and/or within a subterranean reservoir wellbore. Parameters that may be used to assess the effectiveness of the cysteine synthase enzyme may include measurements of cysteine formation kinetics, amount of sulfur-containing compounds present in the recovered downhole fluids and/or subterranean reservoir wellbore before and after treatment with the additive and/or fluid composition, and the like. Methods for measuring these parameters may be used to assess the ability of the cysteine synthase enzyme to reduce, decrease, or inactivate sulfur-containing compounds. 'Effective concentration' is defined herein to mean any concentration of cysteine synthase enzyme that may decrease or reduce the amount of sulfur-containing compounds within the fluid composition, a subterranean reservoir wellbore and a downhole fluid recovered therefrom; alternatively, 'effective concentration' is defined herein to mean any amount of the cysteine synthase enzyme that may decrease the amount of sulfur-containing compounds.

The invention will be further described with respect to the following Examples, which are not meant to limit the invention, but rather to further illustrate the various embodiments.

EXAMPLES

Example 1

Two separate experiments were conducted with two sets of samples where cysteine and $H_2S$ concentrations were measured after completion of each reaction within each sample.

Samples 1 and 5 were the blanks for each set that do not contain cysteine synthase. Samples 2 and 6 included an O-Acetyl-Serine (OAS) in a concentration of 5 mM, pyridoxal-5'-phosphate (PLP) in an amount of 0.25 mM, and a cysteine synthase enzyme, i.e. an O-Acetyl-Serine Sulfhydrylase (OASS) enzyme, in an amount of 50 μL (about 200 nanograms of enzyme). Samples 3 and 7 included OAS in a concentration of 5 mM, PLP in a concentration of 0.25 mM, and the OASS enzyme in an amount of 50 μL. Samples 4 and 8 included OAS in a concentration of 5 mM, no PLP, and the OASS enzyme in an amount of 50 μL.

An increased absorbance measurement at 560 nm represents an increased amount of cysteine formed from each sample. The reactions treated with the cysteine synthase enzyme showed higher concentrations of cysteine compared to the blanks (samples 1 and 5), indicating that the cysteine was synthesized from the enzyme. The cysteine synthase enzyme used $H_2S$ or sulfide during the enzymatic reaction to synthesize cysteine. No significant differences in $H_2S$ reduction (decrease) occurred regardless of whether PLP was present during the enzymatic reaction.

As shown in TABLE 1, each set of samples produced about the same amount of cysteine where the second set produced more cysteine than the first set. Samples 4 and 8, which did not have PLP, produced similar amounts of cysteine indicating that the addition of PLP is optional. The lack of PLP in samples 4 and 8 also indicates that the PLP is optional from the concentrations of $H_2S$ measured, which was the lowest amount of H2S as compared to the other samples 1-3 and 5-7.

Samples 1 and 5, the experiment blanks for each set that did not include the cysteine synthase enzyme, had high amounts (14.5 and 15 mg/L) of $H_2S$ as compared to at least a 50-60% decrease in $H_2S$ present in samples 2-4 and 6-8 treated with the cysteine synthase enzyme.

TABLE 1

Measured Amounts of Cysteine and Sulfide produced form Cysteine Synthase

| Condition | $H_2S$ conc Set 1 | Cysteine Synthesis | $H_2S$ conc Set 2 | Cysteine Synthesis |
|---|---|---|---|---|
| Enzyme Blank | 14.5 mg/L | 0 | 15 mg/L | 0 |
| OAS + Pyridoxal phosphate + enzyme | 8.5 mg/L | 0.223 | 6.5 mg/L | 0.409 |
| OAS + Pyridoxal phosphate + enzyme | 7 mg/L | 0.218 | 6 mg/L | 0.387 |
| OAS + no pyridoxal phosphate + enzyme | 4.5 mg/L | 0.228 | 5 mg/L | 0.458 |

Example 2

Figure 3:
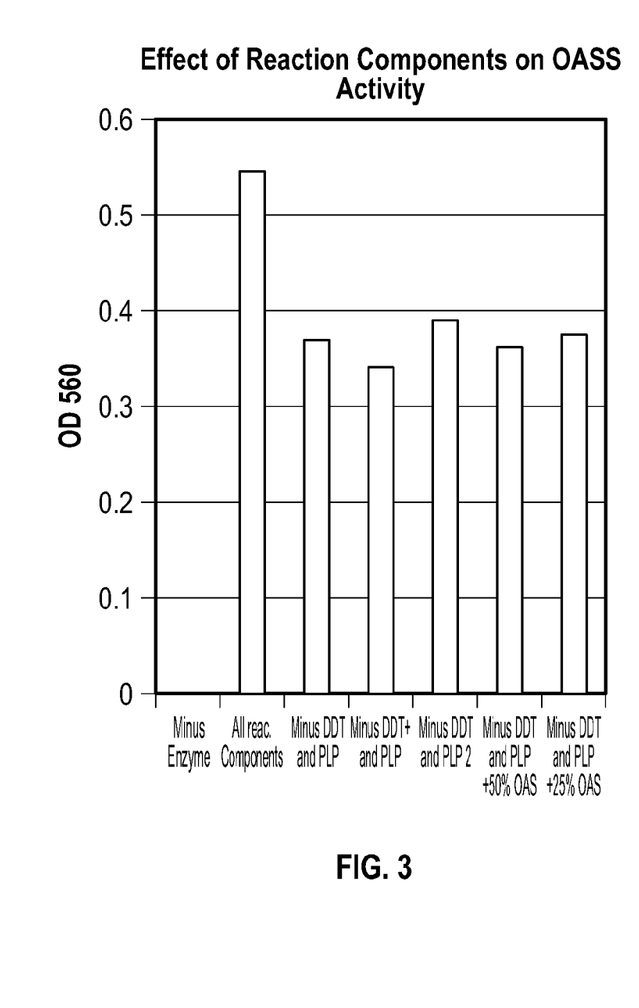
FIG. 3 is a graph depicting the effect of reaction components on cysteine synthase activity where the cysteine formed was treated with acid ninhydrin, and the absorbance was measured with a spectrometer at 560 nm.

FIG. 3 is a graph depicting the effect of reaction components on cysteine synthase activity by detecting the amount of cysteine produced by reacting the completed reaction products with acid ninhydrin and measuring the absorbance with a spectrometer at 560 nm (amino acids reacts with ninhydrin to produce purple color). Sample 1 included 5 mM O-Acetyl serine, 1 mM sulfide, 1 mM DTT, 0.25 mM PLP, and 100 mM Tris HCl buffer, pH 7.5; sample 1 did not include the OASS enzyme. Sample 2 included the cysteine synthase (OASS) enzyme in an amount of 50 microliters μl (about 200 nanograms of the enzyme), 5 mM O-Acetyl serine, 1 mM sulfide, 1 mM DTT, 0.25 mM PLP, and 100 mM Tris HCl buffer, pH 7.5. Sample 3 included the cysteine synthase (OASS) enzyme in an amount of 50 microliters μl, 5 mM O-Acetyl serine, 1 mM sulfide, and 100 mM Tris HCl buffer, pH 7.5; sample 3 did not include dithiothreitol (DTT), nor did sample 3 include PLP. Sample 4 included the cysteine synthase (OASS) enzyme in an amount of 50 microliters μl, 5 mM O-Acetyl serine, 1 mM sulfide, 0.25 mM PLP, and 100 mM Tris HCl buffer, pH 7.5; sample 4 did not include DTT. Sample 5 included the cysteine synthase (OASS) enzyme in an amount of 50 microliters μl, 5 mM O-Acetyl serine, 1 mM sulfide, and 100 mM Tris HCl buffer, pH 7.5; sample 5 did not include dithiothreitol (DTT), nor did sample 3 include PLP. Sample 6 included the cysteine synthase (OASS) enzyme in an amount of 50 microliters μl, 5 mM O-Acetyl serine, 1 mM sulfide, and 100 mM Tris HCl buffer, pH 7.5; sample 6 did not include DTT, nor did sample 6 include PLP; however, sample 6 included 50% O-acetyl-serine OAS. Sample 7 was substantially similar to sample 6, except that sample 7 only included 25% OAS.

As noted from FIG. 3, sample 2, which included all of the reaction components, formed the largest amount of cysteine. Worth noting here, an absence of DTT in the sample may reduce detection of cysteine as the cysteine is oxidized after formation; however, the absence of DTT may not affect the reaction efficiency of the cysteine synthase enzyme. In addition, an absence of PLP in the sample may not affect the reaction efficiency of the cysteine synthase enzyme, as the PLP molecule is added to the cysteine synthase enzyme during protein expression.

Example 3

Figure 4:
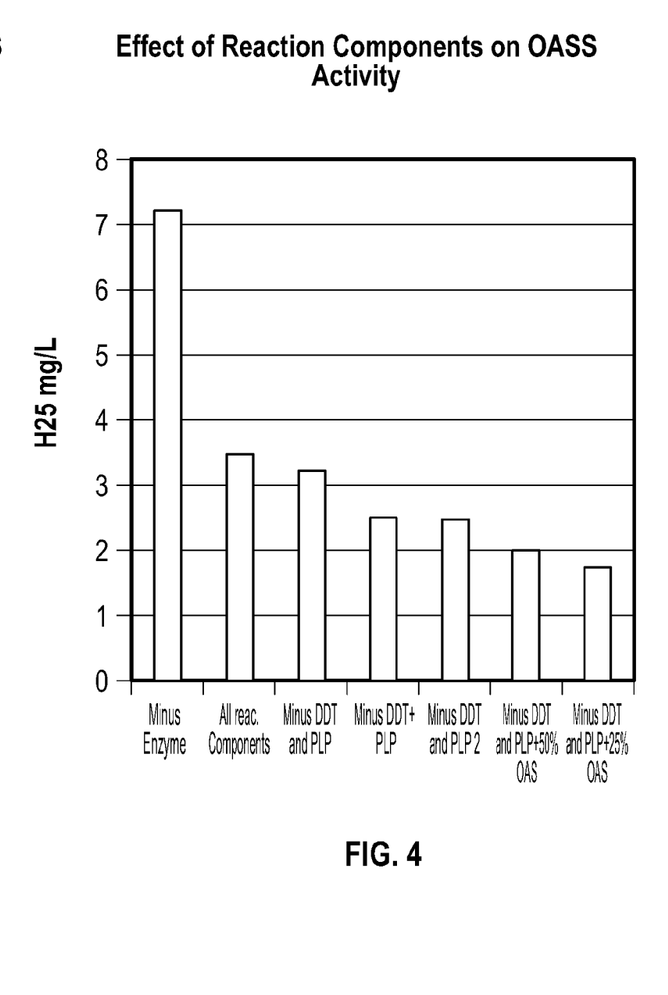
FIG. 4 is a graph depicting the hydrogen sulfide levels measured by colorimetry using an HACH sulfide assay.

FIG. 4 is a graph depicting the amounts of $H_2S$ measured in each sample after 4 h.

Sample 1 included 5 mM O-Acetyl serine, 1 mM sulfide, 1 mM DTT, 0.25 mM PLP, and 100 mM Tris HCl buffer, pH 7.5; sample 1 did not include the cysteine synthase (OASS) enzyme. Sample 2 included the OASS cysteine synthase enzyme in an amount of 50 microliters μl, 5 mM O-Acetyl serine, 1 mM sulfide, 1 mM DTT, 0.25 mM PLP, and 100 mM Tris HCl buffer, pH 7.5. Sample 3 included the cysteine synthase (OASS) enzyme in an amount of 50 microliters μl, 5 mM O-Acetyl serine, 1 mM sulfide, and 100 mM Tris HCl buffer, pH 7.5; sample 3 did not include dithiothreitol (DTT), nor did sample 3 include PLP. Sample 4 included the cysteine synthase (OASS) enzyme in an amount of 50 microliters μl, 5 mM O-Acetyl serine, 1 mM sulfide, 0.25 mM PLP, and 100 mM Tris HCl buffer, pH 7.5; sample 4 did not include DTT. Sample 5 included the cysteine synthase (OASS) enzyme in an amount of 50 microliters μl, 5 mM O-Acetyl serine, 1 mM sulfide, and 100 mM Tris HCl buffer, pH 7.5; sample 5 did not include dithiothreitol (DTT), nor did sample 3 include PLP. Sample 6 included the cysteine synthase (OASS) enzyme in an amount of 50 microliters μl, 5 mM O-Acetyl serine, 1 mM sulfide, and 100 mM Tris HCl buffer, pH 7.5; sample 6 did not include DTT, nor did sample 6 include PLP; however, sample 6 included 50% O-acetylserine OAS. Sample 7 was substantially similar to sample 6, except that sample 7 only included 25% OAS.

As noted from FIG. 4, sample 7 had the lowest amount of $H_2S$ remaining after treatment. The $H_2S$ concentration was decreased the most in samples 6 and 7, which may be due to more efficient use of OAS by the enzyme in the absence of DTT and PLP.

Example 4

Figure 5:
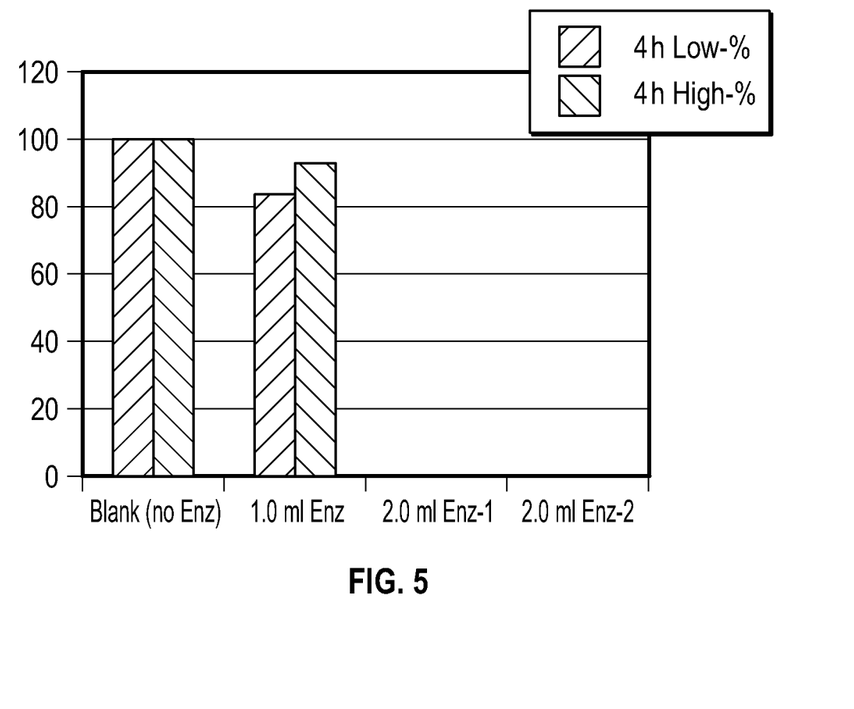

FIG. 5 is a graph depicting the amount of $H_2S$ present in the head space in four samples measured by gas chromatography (GC). 'Head space' refers to the gaseous volume within each sample. Sample 1 was the blank where no cysteine synthase (OASS) enzyme was added to the sample. Samples 2-4 included 400 mL mM Tris-HCL, pH 7.0, 5 mM cysteine synthase, 1 mM DTT, and 0.025 mM PLP. Samples 2-4 were sparged with 10% $H_2S$ for two hours to reach an $H_2S$ concentration of 1500 ppm in the vapor phase. One ml of an cysteine synthase (OASS) enzyme lysate was added to 90 mL of the solution for sample 2, and 2 ml of an OASS cysteine synthase enzyme lysate was added to samples 3 and 4, and then each sample was incubated for 4 hours at 37° C. The cysteine synthase (OASS) enzyme lysate was obtained by the process mentioned above. The $H_2S$ concentration in each sample was then measured by GC.

Two bars are noted for sample 1 and sample 2; the bar on the left for each sample represents the amount of $H_2S$ as detected with a lower sensitivity probe, and the bar on the right for each sample represents the amount of $H_2S$ as detected with a higher sensitivity probe. As noted in FIG. 5, 2 mL of the enzyme lysate of cysteine synthase completely eliminated the $H_2S$ in samples 3-4.

In the foregoing specification, the invention has been described with reference to specific embodiments thereof, and has been described as effective in providing methods, additive compositions, and fluid compositions for decreasing and/or removing hydrogen sulfide in downhole fluids circulated in a subterranean reservoir wellbore. However, it will be evident that various modifications and changes can be made thereto without departing from the broader spirit or scope of the invention as set forth in the appended claims. Accordingly, the specification is to be regarded in an illustrative rather than a restrictive sense. For example, specific base fluids, additional components, pyridoxal phosphates, and the like falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the additive composition for a base fluid, such as a drilling fluid, a completion fluid, a production fluid, a servicing fluid, an injection fluid, a refinery fluid, and combinations thereof may consist of or consist essentially of at least one cysteine synthase enzyme that is at least 75% homologous to the cDNA sequence of SEQ ID NO:1.

The fluid composition may consist of or consist essentially of a base fluid and at least one cysteine synthase enzyme that is at least 75% homologous to the cDNA sequence of SEQ ID NO:1; the base fluid may be or include, but is not limited to a drilling fluid, a completion fluid, a production fluid, a servicing fluid, an injection fluid, a refinery fluid, and combinations thereof.

The method may consist of or consist essentially of circulating a fluid composition into a subterranean reservoir wellbore; the fluid composition may have or include at least one cysteine synthase enzyme that is at least 75% homologous to the cDNA sequence of SEQ ID NO:1 in an effective concentration to decrease and/or remove hydrogen sulfide in downhole fluids.

The words "comprising" and "comprises" as used throughout the claims, are to be interpreted to mean "including but not limited to" and "includes but not limited to", respectively.

What is claimed is:

1. A method comprising:
    circulating a fluid composition into a subterranean reservoir wellbore; wherein the fluid composition comprises at least one cysteine synthase that is at least 75% homologous to the cDNA sequence of SEQ ID NO:1 in an effective concentration to decrease an amount of sulfur-containing compounds; and
    decreasing the amount of sulfur-containing compounds in the subterranean reservoir wellbore and/or downhole fluids recovered therefrom.

2. The method of claim 1, wherein the fluid composition further comprises an additional component selected from the group consisting of a pyridoxal phosphate, O-acetyl-serine, dithiothreitol (DTT), and combinations thereof.

3. The method of claim 1, wherein the fluid composition further comprises at least one sulfur-containing compound; and wherein the fluid composition comprises the sulfur-containing compound in a reduced amount as compared to an identical fluid composition absent the at least one cysteine synthase enzyme.

4. The method of claim 1, further comprising O-acetyl-L-serine in a concentration ranging from about 1 mM to about 20 mM.

5. A method comprising:
    circulating a fluid composition into a subterranean reservoir wellbore; wherein the fluid composition comprises at least one cysteine synthase that is at least 75% homologous to the cDNA sequence of SEQ ID NO:1 in an amount ranging from about 1 nanomolar (nM) independently to about 5 millimolar (mm) as compared to the total base fluid; and
    decreasing the amount of sulfur-containing compounds in the subterranean reservoir wellbore and/or downhole fluids recovered therefrom.

* * * * *